United States Patent [19]

Asai et al.

[11] 4,322,348
[45] Mar. 30, 1982

[54] MAYTANSINOIDS

[75] Inventors: Mitsuko Asai, Osaka; Motowo Izawa, Hyogo; Seiichi Tanida, Kyoto; all of Japan

[73] Assignee: Takeda Chemical Industries, Ltd., Osaka, Japan

[21] Appl. No.: 149,165

[22] Filed: May 14, 1980

[30] Foreign Application Priority Data

Jun. 5, 1979 [JP] Japan .................... 54-70771

[51] Int. Cl.$^3$ .................... C07D 498/18
[52] U.S. Cl. .................... 260/239.3 P; 424/248.54; 435/119
[58] Field of Search .................... 260/239.3 P

[56] References Cited

U.S. PATENT DOCUMENTS 4,162,940  7/1979  Higashide et al.

OTHER PUBLICATIONS

Kupchan et al., "Novel Maytansinoids. Naturally Occurring and Synthetic Antileukemic Esters of Maytansinol[1-3]", Journal of the Amer. Chem. Society, vol. 97, pp. 5294-5295 (1975).

Kupchan et al., "Novel Maytansinoids. Structural Interrelations and Requirements for Antileukemic Activity", Journal of the Amer. Chem. Society, vol. 96, pp. 3706-3708 (1974).

Higashide et al., "Ansamitocin, a group of novel maytansinoid antibiotics with anti properties from Nocardia", Nature, Inter. J. of Science, vol. 270 22/29, pp. 271-722 (Dec. 1977).

Kupchan et al., "The Maytansinoids. Isolation, Structural Elucidation, and Chemical Interrelation of Novel Ansa Macrolides", T. Journal of Organic Chemistry, vol. 42, No. 14, pp. 2349-2357 (Jul. 8, 1977).

Kupchan et al., Journal of Medicinal Chemistry, vol. 21, No. 1, pp. 31-37 (1978).

*Primary Examiner*—Robert T. Bond
*Attorney, Agent, or Firm*—Wegner & Bretschneider

[57] ABSTRACT

Novel Antibiotic C-15003PND, which has the formula:

wherein R represents hydrogen, $-CO-CH_3$, $-CO-CH_2-CH_3$, $$-CO-CH\begin{matrix}CH_3\\CH_3\end{matrix} \quad \text{or} \quad -CO-CH_2-CH\begin{matrix}CH_3\\CH_3\end{matrix},$$

is produced by cultivating a microorganism of the genus Nocardia.

The Antibiotic C-15003PND wherein R is acetyl, propionyl, isobutyryl or isovaleryl is useful for an antifungal, antiprotozoal or antitumor agent and Antibiotic C-15003PND wherein R is hydrogen is useful for an intermediate thereof.

5 Claims, No Drawings

MAYTANSINOIDS

This invention relates to Antibiotic C-15003PND which is a novel antibiotic and a method for producing the same.

The present inventors collected samples, inclusive of a large number of soil samples, and undertook screenings of the microorganisms isolated from such samples for the antibiotic which they might produce. This exploration and investigation resulted in the discoveries that a certain microorganism is able to produce a novel antibiotic, that this microorganism belongs to the genus Nocardia, that cultivating the above microorganism in a suitable nutrient medium under controlled fermentation conditions results in an accumulation of the antibiotic in the culture medium, and that certain derivatives can be obtained from the resulting antibiotic. These findings were followed by further research which has culminated in this invention.

This invention provides a compound represented by the formula (I):

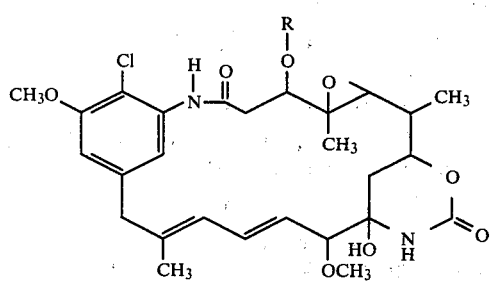

(I)

wherein R represents —CO—CH$_3$, —CO—CH$_2$—CH$_3$,

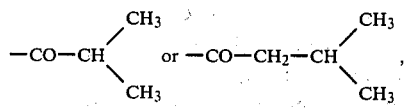

and a method for producing Antibiotic C-15003PND, which has the formula (II):

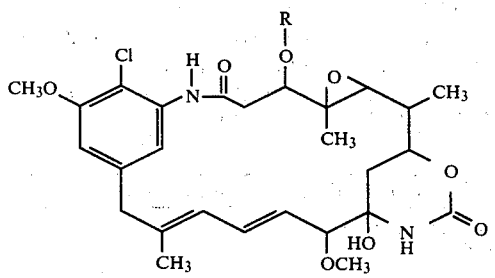

(II)

wherein R represents hydrogen, —CO—CH$_3$, —CO—CH$_2$—CH$_3$,

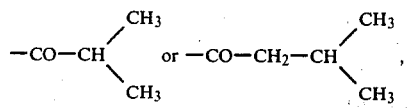

characterized by cultivating a microorganism which belongs to the genus Nocardia and is capable of producing Antibiotic C-15003PND in a culture medium to have Antibiotic C-15003PND elaborated and accumulated in the culture broth and recovering the antibiotic from the culture broth.

In the present invention, the term "Antibiotic C-15003PND" or "C-15003PND" refers generally to five compounds represented by the formula (II) above, or refers to a mixture of any two, three, four or five compounds represented by the formula (II) or a single compound represented by the formula (II).

Also, with respect to the formula (II), the compound wherein R is —CO—CH$_3$ is referred to as "Antibiotic C-15003PND-1" or briefly "C-15003PND-1" or "PND-1", the compound wherein R is —CO—CH$_2$—CH$_3$ is referred to as "Antibiotic C-15003PND-2" or briefly "C-15003PND-2" or "PND-2", the compound wherein R is

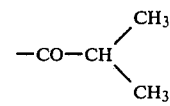

is referred to as "Antibiotic C-15003PND-3" or briefly "C-15003PND-3" or "PND-3", the compound wherein R is

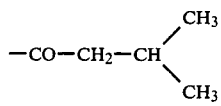

is referred to as "Antibiotic C-15003PND-4" or briefly "C-15003PND-4" or "PND-4" and the compound wherein R is hydrogen is referred to as "Antibiotic C-15003PND-0" or briefly "C-15003PND-0" or "PND-0".

The microorganism which can be used in the present invention may be any type of microorganism so long as it belongs to the genus Nocardia and it is capable of producing Antibiotic C-15003PND.

Among the microorganisms which can be used in the method of this invention are an actinomycete, strain No. C-15003 (hereinafter sometimes referred to briefly as strain No. C-15003) isolated from samples inclusive of soil samples.

The microbiological characteristics of strain No. C-15003 are disclosed in Japanese Patent Application Laid-Open No. 130693/78 (U.S. Pat. No. 4,162,940; Patent Application in the Federal Republic of Germany laid-open as Offenlegungsschrift No. 2,746,209) and, according to the disclosure, strain No. C-15003 was identified as a novel species of microorganism belonging to the genus Nocardia.

The microbiological characters of Strain No. C-15003 are investigated by procedures analogous to those proposed by Shirling & Gottlieb [International Journal of Systematic Bacteriology 16, 313–340 (1966)]. The results of observations at 28° C. over 21 days are as follows.

(1) Morphological Characters

The vegetative mycelium extends well and develops into branches, both on agar and in liquid medium. Many of the hyphae measure 0.8 to 1.2 μm in diameter and, in certain instances, may divide into fragments resembling rod bacteria or branched short lengths of hyphae. The strain gives good growth on various taxonomical media, with aerial mycelium being superimposed on the vegetative mycelium, although it frequently forms coremia like bodies (50-200×200-1000 μm) on which further aerial growth takes place. Many of the aerial mycelia are flexuous, straight or a loosely spiral like configuration being encountered on a few occasions. Microscopic examination of aged cultures reveals that only in few cases the conidia like cells occur in chains, while the cell suspensions obtained from the surfaces of such cultures, as microscopically examined, contained many elongated ellipsoidal (0.8–1.2 μm×4.8–6.8 μm) and ellipsoidal (0.8–1.2×1.0–2.0 μm) bodies resembling arthrospores.

Electron-microscopic examinations show that these bodies have smooth surfaces.

(2) The Constituents of Cells

The strain is shake-cultured in modified ISP No. 1 medium at 28° C. for 66 to 90 hours, at the end of which time the cells are collected and rinsed. By the method of B. Becker et al. [Applied Microbiology 12, 421 (1964)] and the method of M. P. Lechevalier [Journal of Laboratory and Clinical Medicine 71, 934 (1968)], the above whole cells are examined for diaminopimelic acid and sugar composition. The former is found to be the mesoform, while spots are detected which corresponded to galactose and arabinose.

(3) Characteristics on Taxonomical Media

The strain shows comparatively good growth on various media, with the vegetative mycelium being colorless to pale yellow in initial phases of culture and light yellowish tan to yellowish tan in later phases. The strain produces soluble pigments, yellow to yellowish tan, in various taxonomical media. The aerial mycelium is powdery and generally gives moderate growth, being white to yellow or light yellowish tan. The characteristics of the strain in various taxonomical media are set forth below.

Cultural characteristics of Strain No. C-15003 on taxonomical media (A) Sucrose nitrate agar Growth (G): Moderate, Brite Melon Yellow (3 ia)* to Amber tan (3 ic)*, coremia like bodies formed
Aerial mycelium (AM): Scant, white
Soluble pigment (SP): None or pale yellowish tan (B) Glycerol nitrate agar G: Moderate, Lt Ivory (2 ca)*, coremia like bodies formed
AM: Moderate, white
SP: None (C) Glucose asparagine agar G: Moderate, Brite Marigold (3 pa)* to Brite Yellow (2 pa)*.
AM: Scant, white
SP: Brite Yellow (2 pa)*

(D) Glycerol asparagine agar

G: Moderate, Lt Ivory (2 ca)*, coremia like bodies formed
AM: Scant, white
SP: None (E) Starch agar G: Moderate, Lt Ivory (2 ca)* to Lt Wheat (2 ea)*, coremia like bodies formed
AM: Abundant, Lt Ivory (2 ca)*
SP: None (F) Nutrient agar G: Moderate, Lt Ivory (2 ca)* to Colonial Yellow (2 ga)*, coremia like bodies formed
AM: Scant, white
SP: None (G) Calcium malate agar G: Moderate Lt Ivory (2 ca)* to Lt Wheat (2 ea)*, coremia like bodies formed
AM: Moderate, white to Lt Ivory (2 ca)*
SP: None (H) Yeast extract-malt extract agar G: Moderate, Amber (3 lc)* to Brite Yellow (3 la)*, coremia like bodies formed
AM: Moderate, white to Lt Ivory (2 ca)*
SP: None (I) Oatmeal agar G: Moderate, Lt Ivory (2 ca)* to Colonial Yellow (2 ga)*, coremia like bodies formed
AM: Scant, white to light yellow
SP: None (J) Peptone yeast extract iron agar G: Moderate, Colonial Yellow (2 ga)*
AM: None
SP: Colonial Yellow (2 ga)*

(K) Tyrosine agar

G: Moderate, Lt Ivory (2 ca)* to Lt Melon Yellow (3 ea)*, coremia like bodies formed
AM: Moderate, white to Lt Ivory (2 ca)*
SP: Camel (3 ie)*

*The color codes according to Color Harmony Manual, 4th ed. (Container Corporation of America, 1958).

(4) Physiological Characters

The physiological characters of the strain are shown below. Temperature range for growth: 12° C. to 38° C. The temperature range in which good aerial growth occurs on agar (ISP No. 2) is 20° to 35° C.

| The physiological characters of Strain No. C-15003 | |
|---|---|
| Temperature range for growth: | 12 to 38° C. |
| Temperature range for aerial growth: | 20 to 35° C. |
| Liquefaction of gelatin: | Positive |
| Hydrolysis of starch: | Positive |
| Reduction of nitrates: | Positive |
| Peptonization of milk: | Positive |
| Coagulation of milk: | Negative |
| Decomposition of casein: | Positive |
| Production of melanoid pigments: Negative (peptone yeast extract iron agar), positive (tyrosine agar) | |
| Decomposition of tyrosine: | Positive |
| Decomposition of xanthine | Negative |
| Decomposition of hypoxanthine: | Negative |
| Tolerance to lysozyme: | Positive |
| Tolerance to sodium chloride: | 2% |

(5) Utilization of Various Carbon Sources

The utilization of various carbon sources is investigated using a medium described in Pridham and Gottlieb [Journal of Bacteriology 56, 107 (1948)] and a basal medium of the same composition plus 0.1% of yeast extract. The resultant spectrum is shown below.

| The utilization of carbon sources by Strain No. C-15003 | | | |
|---|---|---|---|
| Source of carbon | Growth | Sources of carbon | Growth |
| D-Xylose | + | ++* Raffinose | ± ±* |
| L-Arabinose | + | + Melibiose | + + |
| D-Glucose | ++ | ++ i-Inositol | − − |
| D-Galactose | + | + D-Sorbitol | − − |
| D-Fructose | +++ | ++ D-Mannitol | ++ ++ |
| L-Rhamnose | + | + Glycerol | − ± |
| D-Mannose | +++ | ++ Soluble starch | + + |
| Sucrose | ++ | ++ Control | − − |
| Lactose | − | − | |
| Maltose | ± | + | |
| Trehalose | + | ++ | |

*Basal medium with 0.1% yeast extract added
Note:
+ + +: Luxuriant growth
+ +: Good growth
+: Growth
±: Poor growth
−: No growth

(6) Other Characteristics

The cells are harvested by the procedure previously described in (2) and DNA is prepared by a procedure analogous to that of J. Marmur et al. [Journal of Molecular Biology 3, 208, 1961]. The G-C (Guanine-Cytosine) content of the DNA is found to be about 71 mole %.

Gram-staining of the vegetative mycelium of this strain is positive.

The above characteristics of Strain No. C-15003 are compared with the descriptions in S. A. Waksman's "The Actinomycetes Vol. 2" [The Williams and Wilkins Co., 1961]; R. E. Buchanan and N. E. Gibbons, "Bergey's Manual of Determinative Bacteriology, 8th ed, 1974"; and other literature references.

Whilst this strain was thought to belong to Group III of the genus Nocardia, the failure to find any species having the characters so far described among the known strains led us to conclude that this strain represented a novel species of microorganism.

The above strain, Nocardia sp. No. C-15003, was deposited in the Fermentation Research Institute, Agency of Industrial Science and Technology, Japan as FERM-P No. 3992 on Mar. 23, 1977; the Institute for Fermentation, Osaka, Japan, as IFO 13726 on Mar. 22, 1977; and The American Type Culture Collection, U.S.A. as ATCC 31281 on Mar. 31, 1977. The strain Nocardia sp. No. C-15003 (ATCC 31281) is described in The American Type Culture Collection Catalogue of Strains I Fourteenth Edition 1980.

The microorganisms of the genus Nocardia are liable, as a general trait, to undergo variations and mutations, whether spontaneously or under the influence of a mutagen. For example, the many variants of the strain which are obtainable by irradiation with X-rays, gamma rays, ultraviolet light, etc., by monocell isolation, by cultivating on media containing various chemicals, or by any other mutagenic treatment, as well as the mutants spontaneously derived from the strain, should not be considered to represent any other distinct species but, rather, any of such variants and mutants, unless they are sufficiently different and distinct to be identified as different species in reference to the above and hereinafter described microbiological properties and if they are capable of elaborating Antibiotic C-15003PND, may be invariably utilized for the purposes of the present invention. By way of example, subjecting the above-described strain to various mutagenic treatments yields variants which substantially do not produce soluble pigments, variants which give colorless vegetative mycelia, variants which give yellowish green vegetative mycelia, variants which give reddish brown or orange red vegetative mycelia, variants whose mycelia are ready to be fragmented into rods or branched short mycelia, or variants which give abundant aerial mycelia which are white in color.

The medium used for the cultivation of the Antibiotic C-15003PND-producing microorganism may be either a liquid or a solid medium as long as it contains nutrients which the strain may utilize, although a liquid medium is preferred for high-production purposes. The medium should contain certain additives used in the present invention as well as carbon and nitrogen sources which can be assimilated or digested by the Antibiotic C-15003PND-producing microorganism, inorganic substances, trace nutrients, etc. Examples of carbon sources are glucose, lactose, sucrose, maltose, dextrin, starch, glycerol, mannitol, sorbitol, fats and oils (e.g., soybean oil, lard oil, chicken oil, etc.) and the like. Examples of nitrogen sources are meat extract, yeast extract, dried yeast, soybean meal, corn steep liquor, peptone, cottonseed flour, spent molasses, urea, ammonium salts (e.g., ammonium sulfate, ammonium chloride, ammonium nitrate, ammonium acetate, etc.) and the like. The medium may further contain salts of sodium, potassium, calcium, magnesium, etc., salts of iron, manganese, zinc, cobalt, nickel, etc., salts of phosphoric acid, boric acid, etc. and organic acid salts such as acetates, propionates, etc. Further, the medium may contain various amino acids (e.g., glutamic acid, aspartic acid, alanine, glycine, lysine, methionine, proline, etc.), peptides (e.g., dipeptides, tripeptides, etc.), vitamins (e.g., $B_1$, $B_2$, nicotinic acid, $B_{12}$, C, E, etc.), nucleic acids (e.g., purine, pyrimidine and derivatives thereof) and the like. For the purpose of adjusting the pH of the medium, there may be added an inorganic or organic acid, an alkali, a buffer solution or the like. Suitable amounts of oils, fats, surfactants, etc. may also be added to the medium as antifoams.

The cultivation may be conducted by any of the stationary, shake, submerged aerobic and other cultural methods. For high production runs, submerged aerobic culture is of course preferred. While the conditions of cultivation vary depending upon the compositions of medium, the type of strain, cultural method and other factors, it is normally preferred to carry out incubation at about 20° to 35° C. with an initial pH of about neutral. Particularly desirable is a temperature from about 23° C. to 30° C. in an intermediate stage of cultivation, with an initial pH of about 6.5 to 7.5. While the incubation time also varies depending upon the same factors as described above, it is advisable to continue the incubation until the titer of the desired antibiotic becomes maximal. In the case of shake culture or aerobic submerged culture in a liquid medium, the time required normally ranges from about 48 to 240 hours.

In order to isolate C-15003PND-4, PND-3, PND-2, PND-1 and/or PND-0 from the culture broth, since the compounds of this invention are neutral and oil-soluble, isolation and purification procedures which are normally utilized in the recovery of metabolites from microbial cultures can be advantageously utilized. For example, a means utilizing the difference in solubility between the compounds of this invention and impurities, a means utilizing differences in adsorption affinity with respect to various adsorbents such as activated carbon, macroporous non-ionic resins, silica gel, alumina and the like, a means for removing impurities by ion-exchange resins can be used alone or in combination or in repeated use. As described above, since C-15003PND-4, PND-3, PND-2, PND-1 and PND-0 are produced in both the liquid phase of the culture broth and the microbial cells, these adsorbents are used for the liquid phase directly or after solvent extraction of the liquid phase and, for microbial cells, these adsorbents can be used after solvent extraction in order to isolate the antibiotics by adsorption. In case of solvent extraction, either (1) solvent extraction of the entire culture broth from which microbial cells have not been separated or (2) solvent extraction of each of the mycelium and the liquid phase of culture broth, after filtration or centrifugation, can be employed. In extracting the liquid phase (filtrate) and microbial cells separately, the following procedure can be practiced advantageously.

Solvents which can be suitably used for extraction from the filtrate are organic solvents which are immiscible with water, for example, aliphatic acid esters such as ethyl acetate, amyl acetate and the like, alcohols such as butanol and the like, halogenated hydrocarbons such as chloroform and the like, ketones such as methyl isobutyl ketone and the like. The extraction is carried out near a neutral pH and is preferably achieved using ethyl acetate from the fermentation filtrate adjusted to pH 7. The extract is washed with water, concentrated under reduced pressure and a non-polar solvent such as petroleum ether, n-hexane and the like is added to the residue to recover a crude substance containing an active component.

In case of using a macroporous adsorbent resin as a means for recovering the above crude substance, C-15003PND may be separated by elution with a mixture of a lower alcohol, a lower ketone or an ester with water. Examples of said lower alcohol are methanol, ethanol, propanol, butanol and the like, examples of said lower ketone are acetone, methyl ethyl ketone and the like, and examples of said ester are ethyl acetate and the like. As an example, the filtrate of culture broth or the extract of microbial cells is passed through a column of Diaion HP-10 (Mitsubishi Chemical Industries Limited, Japan) to adsorb active components and, after washing with 60% aqueous methanol, the column is eluted with 90% aqueous methanol to obtain a crude substance containing the active components. The resulting substance shows a number of spots on TLC which are assignable to substances other than Antibiotic C-15003PND, and the following purification procedures can be used stepwise. That is, a wide variety of adsorption chromatography and partition chromatography can be used effectively as purification procedures employed normally. As examples of adsorbents, a carrier generally used, for example, silica gel, alumina, macroporous non-ionic adsorbent resins can be used, and as partition chromatography, a reversed phase partition gel can be used. However, for purification of the crude substance, silica gel is most effectively used and Antibiotic C-15003PND can be eluted first with a halogen-containing hydrocarbon such as dichloromethane, chloroform and the like and then adding a polar solvent, for example, an alcohol such as ethanol, methanol and the like, a ketone such as acetone, methyl ethyl ketone and the like. In an embodiment, column chromatography is performed using a silica gel (Merck, Germany) as a carrier and with a solvent admixed with incremental ratios of methanol to chloroform. The eluate is assayed by thin-layer chromatography (hereinafter referred to as "TLC") and the fractions containing C-15003PND and coproduced ansamitocins are pooled, concentrated under reduced pressure. Ansamitocins, which is described in Nature vol. 270, pp. 271–272 (1977); Japanese Patent Application Laid-Open No. 130693/1978; U.S. Pat. No. 4,162,940; Patent Application in the Federal Republic of Germany laid-open as Offenlegungsschrift No. 2,746,209, are crystallized from ethyl acetate and removed by filtration.

Since the filtrate contains C-15003PND and still other impurities, it is subjected to the subsequent purification procedure, for example, to the second silica gel column chromatography using a different solvent system. In this instance, the column is developed starting with a non-polar solvent, for example, petroleum ether, n-hexane, etc. and then adding a polar solvent such as ethyl acetate, acetone, ethanol and the like whereby C-15003PND is eluted. The fractions which are found to contain C-15003PND by TLC analysis are collected, concentrated under reduced pressure and crystallized from ethyl acetate to obtain crystals containing C-15003PND. The combination of solvents used for the first and second silica gel columns can be in a reverse order and further the carrier can be substituted by alumina. Also, organic solvents which are normally used can be suitably used in combination. The crystals thus obtained also contain, in addition to C-15003PND, ansamitocin P-4 and P-3, maytansinol propionate and maytanacine [Journal of the American Chemical Society, Vol. 97, 5294 (1975)]. In the case of PND-0, as the crystal thus obtained also contains maytansinol, the crystals is subjected to recrystallization from methanol to obtain PND-0 crystal and maytansinol remains in the mother liquor.

In order to isolate C-15003PND-1, PND-2, PND-3 and PND-4 from these crystals, it is advantageous to use a reversed phase partition gel. The solvent for elution can be a water-miscible alcohol or ketone. An example of the procedure comprises preparative separation using the high performance liquid chromatography Prep LC/System 500 (Waters Associates Inc. U.S.A.) with a reversed phase gel $C_{18}$ (Waters Associates Inc. Prep PAK-500/$C_{18}$). When aqueous methanol is used as a solvent, C-15003PND-1, PND-2, PND-3 and PND-4 are eluted in that order and, after analysis of each fraction by a reversed phase TLC, each of the fractions of C-15003PND-4, PND-3, PND-2 and PND-1 is concentrated under reduced pressure. The resulting concentrate is further extracted with ethyl acetate, and the extract is concentrated under reduced pressure and petroleum ether is added to the residue to obtain a white powder.

The physical and chemical properties of C-15003PND-1 obtained in Example 10, C-15003PND-2 obtained in Example 9, C-15003PND-3 obtained in Example 8 and C-15003PND-4 obtained in Example 7 are shown in Table 1 below.

TABLE 1

| | C-15003PND-1 $C_{29}H_{37}ClN_2O_9$ = 593.089 | C-15003PND-2 $C_{30}H_{39}ClN_2O_9$ = 607.115 | C-15003PND-3 $C_{31}H_{41}ClN_2O_9$ = 621.141 | C-15003PND-4 $C_{32}H_{43}ClN_2O_9$ = 635.167 |
|---|---|---|---|---|
| Appearance | White powder | White powder | White powder | White powder |
| Optical rotation $[\alpha]_D^{22}$ (in ethanol) | $-55.8° \pm 10°$ (c = 0.12) | $-56.3° \pm 10°$ (c = 0.14) | $-57.1° \pm 10°$ (c = 0.14) | $-56.6° \pm 10°$ (c = 0.415) |
| Elemental analysis Found (%) | C 58.34 H 6.52 N 4.66 Cl 5.81 | C 59.10 H 6.72 N 4.77 Cl 5.68 | C 59.63 H 6.82 N 4.67 Cl 5.38 | C 60.04 H 6.97 N 4.37 Cl 5.44 |
| Elemental analysis Calculated (%) | C 58.79 H 6.29 N 4.72 Cl 5.98 | C 59.35 H 6.48 N 4.61 Cl 5.84 | C 59.94 H 6.65 N 4.51 Cl 5.71 | C 60.51 H 6.82 N 4.41 Cl 5.58 |
| Ultraviolet absorption spectrum nm ($\epsilon$) (in methanol) | 232 (31500) 239 (32000) 252 (sh28600) 279 (3780) 288 (3700) | 232 (31000) 239 (32000) 252 (sh28200) 279 (3800) 288 (3760) | 232 (32500) 239 (33000) 252 (sh28400) 279 (3880) 288 (3790) | 232 (sh 31500) 239 (31100) 252 (sh 27600) 279 (3760) 288 (3690) |

| | PND-1 | PND-2 | PND-3 | PND-4 |
|---|---|---|---|---|
| Infrared absorption spectrum ($cm^{-1}$) (KBr) | 1740, 1730, 1590, 1455, 1425, 1390, 1145, 1100, 1080 | 1740, 1730, 1590, 1455, 1425, 1390, 1145, 1100, 1080 | 1740, 1730, 1590, 1455, 1425, 1390, 1145,1100 1080 | 1740, 1730, 1590, 1455, 1425, 1390, 1145, 1100, 1080 |
| Nuclear magnetic resonance spectrum (ppm) 90 MHz, $CDCl_3$ | 1.13(3H,s) 1.24(3H,d) 1.76(3H,s) 3.38(3H,s) 3.95(3H,s), others | 1.12(3H,s) 1.26(3H,d) 1.76(3H,s) 3.37(3H,s) 3.95(3H,s), others | 1.10(3H,s) 1.20(3H,d) 1.75(3H,s) 3.35(3H,s) 3.95(3H,s), others | 1.14(3H,s) 1.26(3H,d) 1.76(3H,s) 3.39(3H,s) 3.94(3H,s), others |
| Mass spectrum (m/e) | 592, 577, 531, 471, 456, 436, | 606, 591, 545, 471, 456, 436 | 620, 605, 559, 471, 456, 436 | 634, 619, 573, 471, 456, 436 |
| Solubility | Insoluble in petroleum ether, n-hexane, water. Soluble in chloroform, ethyl acetate, acetone, ethanol, methanol, pyridine, tetrahydrofuran, dimethyl sulfoxide. | Insoluble in petroleum ether, n-hexane, water. Soluble in chloroform, ethyl acetate, acetone, ethanol, methanol, pyridine, tetrahydrofuran, dimethyl sulfoxide. | Insoluble in petroleum ether, n-hexane, water. Soluble in chloroform, ethyl acetate, acetone, ethanol, methanol, pyridine, tetrahydrofuran, dimethyl sulfoxide. | Insoluble in petroleum ether, n-hexane, water. Soluble in chloroform, ethyl acetate, acetone, ethanol, methanol, pyridine, tetrahydrofuran, dimethyl sulfoxide. |
| Color reactions | Dragendorff Reagent: Positive. Beilstein Reaction: Positive. | Dragendorff Reagent: Positive. Beilstein Reaction: Positive. | Dragendorff Reagent: Positive. Beilstein Reaction: Positive. | Dragendorff Reagent: Positive. Beilstein Reaction: Positive. |
| Thin-layer chromatography ($R_f$) (1)Merck silica gel | (1) Chloroform-methanol (9:1), 0.45 | (1) Chloroform-methanol (9:1), 0.47 | (1) Chloroform-methanol (9:1), 0.49 | (1) Chloroform-methanol (9:1), 0.51 |
| (2)Merck silica gel | (2) Ethyl acetate saturated with water, 0.37 | (2) Ethyl acetate saturated with water, 0.42 | (2) Ethyl acetate saturated with water, 0.48 | (2) Ethyl acetate saturated with water, 0.55 |
| Reversed phase Thin-layer chromatography ($R_f$) (3)Merck Rp-18$F_{254}$ | (3) 80% Aqueous methanol, 0.64 | (3) 80% Aqueous methanol, 0.61 | (3) 80% Aqueous methanol, 0.58 | (3) 80% Aqueous methanol, 0.55 |

The physical and chemical properties of C-15003PND-0 obtained in Example 11 are shown below:

C-15003PND-0, $C_{27}H_{35}ClN_2O_8 = 551.050$
(1) Appearance: Colourless needles
(2) m.p: 189°–191° C.
(3) Optical rotation: $[\alpha]_D^{22}$-128°±10° (c=0.25 $CHCl_3$)
(4) Elemental analysis: Found: C, 58.59; H, 6.62; N, 4.81; Cl, 6.27. Calculated: C, 58.85; H, 6.40; N, 5.08; Cl, 6.43.
(5) Ultraviolet absorption spectrum [nm (ε) in methanol]: $\lambda_{max}^{MeOH}$ 231(32500), 239(32500), 250(sh 28400), 278(4060), 287(3900).
(6) Infrared absorption spectrum ($cm^{-1}$, KBr): 1675, 1590, 1430, 1393, 1304, 1178, 1093, 1063.
(7) Nuclear magnetic resonacce spectrum (ppm, 90 MHz, $CDCl_3$): δ0.98(3H, s), 1.27(3H, d), 1.67(3H, s), 3.33(3H, s), 3.92(3H, s), others
(8) Mass spectrum (m/e): 550, 489, 471, 456, 454
(9) Solubility:
Insoluble in petroleum ether, n-hexane, water.
Soluble in chloroform, ethyl acetate, acetone, ethanol, pyridine, tetrahydrofuran, dimethyl sulfoxide.
(10) Color reaction:
Dragendorff reagent = positive
Beilstein reaction = positive
(11) Thin layer chromatography ($R_f$):
 (i) Merck silica gel, chloroform-methanol (9:1): 0.30
 (ii) Merck silica gel, ethyl acetate saturated with water: 0.25
(12) Reversed phase thin-layer chromatography ($R_f$):
Merck $R_p$-18$F_{254}$, 80% aqueous methanol: 0.61

From the above physico-chemical properties and the antimicrobial and antitumor activities hereinafter described as well as other properties, the compounds of this invention are easily supposed to have a structure similar to that of ansamitocin. In the mass spectra of C-15003PND-1, PND-2, PND-3, and PND-4, m/e 471, 456 and 436 are observed as common mass numbers and, thus, these compounds are considered to have the same structural skeleton but different ester residual groups as side chains. Also, the characteristic fragment peaks $M^+ - a$ (a=NHCO.$H_2O$) and $M^+ - (a+b)$ (b=R—OH) which are observed in maytansinoids are as follows:

|  | $M^+ - a$ | $M^+ - (a + b)$ | b |
|---|---|---|---|
| C-15003PND-1 | 531 | 471 | 60 |
| C-1500PND-2 | 545 | 471 | 74 |
| C-15003PND-3 | 559 | 471 | 88 |
| C-15003PND-4 | 573 | 471 | 102 |
| C-15003PND-0 | 489 | 471 | 18 |

Thus, the ester residual groups at the 3-position appear to be acetyl in C-15003PND-1, propionyl in C-15003PND-2, isobutyryl in C-15003PND-3 and isovaleryl in C-15003PND-4. In comparing C-15003PND-3 with the corresponding ansamitocin P-3 (Antibiotic C-15003P-3), ansamitocin P-3 shows $M^{30}$—a 573 and $M^+ - (a+b)$ 485, whereas C-15003PND-3 shows each mass unit 14 less than that of ansamitocin P-3 and, therefore, C-15003PND-3 is supposed to be a compound where one methyl group in the skeleton moiety of ansamitocin P-3 has been converted into hydrogen. Further, in comparing nuclear magnetic resonance spectra, ansamitocin P-3 shows signals at δ3.18, 3.38 and 4.00 assignable to methyl groups, whereas the signal at δ3.18 disappears in C-15003PND-3, indicating that C-15003PND-3 is a compound wherein the N—$CH_3$ group at $C_{18}$ has been converted into an NH group.

The above analysis can also be applied to C-15003PND-4, PND-2, PND-1 and PND-0. From the above data, the presumptive structures of C-15003PND-1, PND-2, PND-3, PND-4 and PND-0 are shown in FIG. 1 below.

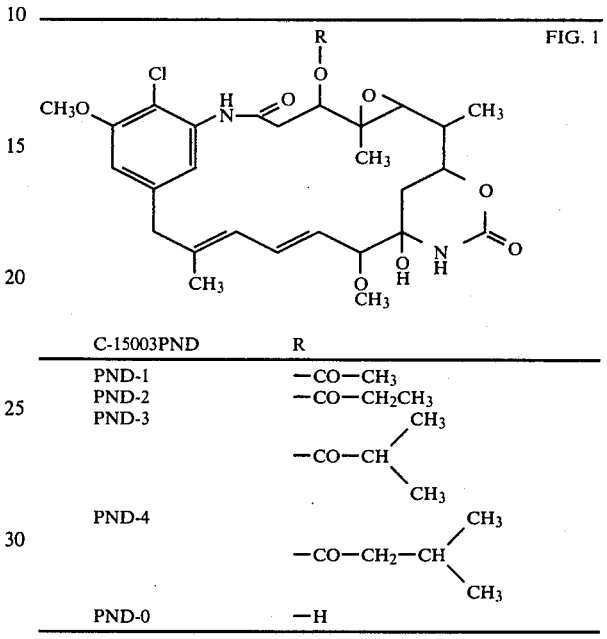

FIG. 1

| C-15003PND | R |
|---|---|
| PND-1 | —CO—$CH_3$ |
| PND-2 | —CO—$CH_2CH_3$ |
| PND-3 | —CO—CH(CH$_3$)$_2$ |
| PND-4 | —CO—$CH_2$—CH(CH$_3$)$_2$ |
| PND-0 | —H |

Each of the compounds having the above formula is a novel compound and exhibits antitumor and antifungal activities as hereinafter described and, in addition, they can be used as starting materials for producing certain useful derivatives.

BIOACTIVITY

(A) Antimicrobial Activity

The growth inhibitory activity of the compounds against the test organisms is assayed by the paper disc method using a trypticase soy agar (manufactured by Baltimore Biologicals Laboratories, U.S.A.) as the assay medium. That is, the growth inhibitory activity is determined on the plate medium containing the following test organisms using a paper disc (manufactured by Toyo Seisakusho Co. Ltd., thin type, 8 mm in diameter) impregnated with 0.02 ml of a 300 μg/ml solution of C-15003PND-1, PND-2, PND-3 or PND-4. As a result, these compounds do not show any activity against the following test organisms: *Escherichia coli, Proteus vulgaris, Proteus mirabilis, Pseudomonas aeruginosa, Staphylococcus aureus, Bacillus subtillis, Bacillus cereus, Klebsiella pneumoniae, Serratia marcescens* and *Mycobacterium avium*.

Also, the compounds are assayed by the paper disc method using an agar plate [3.5 g of disodiumhydrogen phosphate, 0.5 g of potassium dihydrogen phosphate, 5 g of yeast extract (manufactured by Difco Co.), 10 g of glucose, 15 g of agar, 1000 ml of distilled water, pH 7.0] as a medium for assay and *Hamigera avellanea* IFO 7721 as a test organism. Thus, the growth inhibitory activity is determined on the plate medium containing the test organism using a paper disc (Toyo Seisakusho Co. Japan, thin type, 8 mm in diameter) impregnated with 0.02 ml of a 100 μg/ml solution of C-15003PND-1, PND-2, PND-3 or PND-4. As a result, C-15003PND-1, PND-2, PND-3 and PND-4 show inhibitory zones of 28 mm, 30 mm, 34 mm and 36 mm, respectively.

Further, the growth inhibitory activity of these antibiotics is determined by the liquid dilution method using a medium [20 g of proteose peptone (Difco Co.), 1 g of yeast extract, 2 g of glucose, 1000 ml of distilled water, 10 ml of 1 M phosphate buffer pH 7.0] and *Tetrahymena pyriformis* W as a test organism with incubation at 28° C. for 44 to 48 hours. As a result, the growth of the above test organism is found to be inhibited at a concentration of 8 μg/ml of C-15003PND-1, 4 μg/ml of C-15003PND-2, 2 μg/ml of C-15003PND-3 and 1 μg/ml of C-15003PND-4.

(B) Antitumor Activity

The therapeutic effects of C-15003PND-1, PND-2, PND-3 and PND-4 on tumor cells leukemia P388 ($1 \times 10^6$ cells/mouse, transplanted intraperitoneally) are determined by administering the compound intraperitoneally for 9 consecutive days. As a result, a life-prolonging effect due to the administration of compound is observed in the test mouse.

(C) Toxicity

In an acute toxicity test in mice, each of C-15003PND-1, PND-2, PND-3 and PND-4 is intraperitoneally administered and the estimated $LD_{100}$ and $LD_0$ of these antibiotics are found to be 2.5 mg/kg and 0.313 mg/kg, respectively.

As described above, the present compound (I) has strong inhibitory activity against fungi and protozoa and, therefore, is also useful as antifungal or antiprotozoal agent. Further, the compound (I) exhibits a life-prolonging effect in tumor-bearing mammals (e.g., mice, etc.) and, therefore, is expected to be useful as an antitumor agent.

The compound (I) can be used advantageously as antifungal and antiprotozoal agents, for example, in studying the bacterial bionomy in soils, activated sludge or animal body fluids. Thus, in separating useful bacteria from soil samples or in studying the action of bacteria to the exclusion of protozoa and fungi in connection with the operation and analysis of active sludge processes for waste water treatment, it is possible to ensure a selective growth of bacterial flora, not permitting growth of the concomitant fungi and protoza. More specifically, a test sample is added to a liquid or solid medium and 0.1 ml of an aqueous solution containing 1% methanol and 10 to 100 μg/ml of the antibiotic of the present invention is added to the medium, followed by incubation.

The compound (I) has a life-prolonging effect on tumor-bearing warm-blooded mammals (e.g., mice, rat, dog, cat, etc.) and, therefore, can be used as an antitumor agent. In using the compound (I) as an antitumor agent, it can be administered parenterally or orally. In parenteral administration, the compound is preferably used as injections, e.g. by the subcutaneous, intraperitoneal, intravenous or intramuscular route. The dose level can range, for example from about 5 to about 800 μg/kg of body weight at a single dose and can be suitably varied depending on the severity of conditions and the species of animals to be treated. The solution for injection may be prepared by a conventional procedure, for example, by dissolving the compound (I) in an alcohol (e.g., methanol, ethanol) in proportion of about 50 μg to 300 μg of the compound (I) in about 0.5 ml of the alcohol and adding a physiological saline solution in a proportion sufficient to make a total volume of 10 ml. When the amount to be administered in small, a solution for injection can be prepared by diluting the above solution with a further amount of physiological saline.

C-15003PND-0 is useful for an intermediate for producing a usable medicine. For example, C-15003PND-0 is subjected to acylation employing a corresponding carboxylic acid anhydride for example isobutyric anhydride, and the acylation gives C-15003PND in which R is other than hydrogen.

The present invention is further illustrated in greater detail by the following Examples and a Reference Example.

EXAMPLE 1

Nocardia sp. No. C-15003 which has been cultivated on a yeast extract-malt extract agar slant is used to inoculate 40 ml of a seed medium containing 2% glucose, 3% soluble starch, 1% soybean flour, 1% corn steep liquor, 0.5% Polypepton, 0.3% NaCl and 0.5% $CaCO_3$, pH 7.0, in a 200 ml Erlenmeyer flask and the flask is cultivated at 28° C. on a rotary shaker for 48 hours to produce a seed culture.

0.5 ml of the seed culture thus obtained is then transferred to 40 ml of a main culture medium containing 5% dextrin, 3% corn steep liquor, 0.1% Polypepton and 0.5% $CaCO_3$, pH 7.0, in a 200 ml Erlenmeyer flask and the flask is cultivated at 28° C. for 90 hours on a rotary shaker. The culture broth exhibits the productivity of 25 μg/ml as a total titer including ansamitocins when it is assayed by the liquid dilution method against *Tetrahymena pyriformis* W as a test organism using ansamitocin P-3 as a standard.

EXAMPLE 2

10 ml of the culture broth obtained in Example 1 is transferred to a 2 l Sakaguchi flask containing 500 ml of the seed medium and the flask is cultivated at 28° C. for 48 hours on a reciprocal shaker. 1000 ml of the resulting culture broth is transferred to a 500 l stainless steel tank containing 300 l of the seed medium and cultivated under conditions of 28° C., aeration at 300 l/minute, stirring at 200 r.p.m. (⅓ DT), and internal pressure 1 kg/cm² for 48 hours to obtain a seed culture broth. The 200 l of the resulting seed culture broth is then transferred to a 6000 l stainless steel tank containing 4000 l of a main culture medium having the same composition as described in Example 1 and cultivated under conditions of 28° C., aeration at 2000 l/minute, stirring at 80 r.p.m. (½ DT) and internal pressure of 1 kg/cm² for 90 hours. The resulting culture broth is assayed in the same manner as described in Example 1 and exhibits the productivity of 25 μg/ml as a total titer including ansamitocins.

EXAMPLE 3

To 3800 l of the culture broth obtained as described in Example 2 is added 20 kg of Hyfro-Supercel (Johns-Manville Product Co., U.S.A.), followed by thorough stirring. The resulting mixture is filtered through a filter press to obtain 3400 l of a filtrate and 320 kg of microbial cells. 1000 l of ethyl acetate is added to 3400 l of the filtrate followed by stirring to effect extraction and this procedure is repeated twice. The ethyl acetate layers are combined, washed twice with 700 l portions of 1/5 M aqueous sodium carbonate and then with water and concentrated under reduced pressure to a volume of 1 l. Petroleum ether is added to the residue and the resulting precipitate is filtered (104 g). 200 ml of chloroform is added to the resulting crude substance followed by stirring and any insoluble material is removed by filtration. 100 g of silica gel (Merck, Germany, Art. 7734, 0.05–0.2 mm) is added to the filtrate followed by stirring, and the chloroform is distilled off under reduced pressure. The residue is placed at the top of a previously prepared silica gel column (2000 ml), and 2000 ml of chloroform, 4000 ml of chloroform-methanol (25:1) and 4000 ml of chloroform-methanol (9:1) are passed through the column to fractionate the eluate into 400 ml fractions. Each of the fractions is spotted at a position of 2.5 cm from the bottom edge of a silica gel glass plate (Merck, Germany, Art-5715, 0.25 mm, 20×20) and developed with a solvent system of chloroform-methanol (9:1) to a distance of about 17 cm. After development, the absorbed pattern is analyzed under irradiation with ultraviolet rays (at 2537 Å) and fraction Nos. 9 to 13 (Fraction I) and No. 22 (Fraction II), showing an absorption at about $R_f$ 0.45 to 0.50 and $R_f$ 0.30, are collected and concentrated under reduced pressure to a volume of about 50 ml, respectively. 300 ml of petroleum ether is added to the Fraction I and II concentrates to obtain 53 g (crude I) and 460 mg (crude II) of a crude substances, respectively. 200 ml of ethyl acetate is added to 53 g of the resulting crude substance (crude I) to dissolve the substance and the solution is allowed to stand to precipitate co-produced ansamitocin which is then filtered (31 g). The resulting filtrate is concentrated under reduced pressure, and 30 ml of ethyl acetate and 20 ml of diethyl ether are added to dissolve the residue, followed by allowing the solution to stand to crystallize a second crop of ansamitocin (3 g). The second filtrate is concentrated under reduced pressure to a volume of 30 ml and 150 ml of petroleum ether is added thereto to obtain 12.1 g of a yellow powder from the mother liquor of second crystals.

EXAMPLE 4

500 l of 70% aqueous acetone is added to 320 kg of the microbial cells obtained as described in Example 3, followed by stirring to effect extraction and thereafter the mixture is filtered through a filter press. Extraction with 500 l of 70% aqueous acetone is repeated again, and the filtrates obtained by filtration as described above are combined and concentrated under reduced pressure to distill off the acetone. The resulting aqueous solution is absorbed on a column of 25 l of Diaion HP-10 (Mitsubishi Chemical Industries Ltd., Japan) and, after washing the column with 50 l of water and 50% aqueous methanol, the elution is carried out with 75 l of 90% aqueous methanol. The eluate is concentrated under reduced pressure to 8 l and shaken with 10 l of water and 10 l of ethyl acetate. The above concentration and shaking are repeated. The ethyl acetate layer are combined, washed with water, dried over anhydrous sodium sulfate and concentrated under reduced pressure. The precipitate formed by adding petroleum ether is separated by filtration (47 g). The resulting crude substance is purified by a silica gel column in the same manner as described in Example 3 to obtain 12.3 g of crude I and 85 mg of crude II. The crude I is crystallized first from ethyl acetate and then from ethyl acetate-ether to obtain 6.3 g of ansamitocin crystals as a first crop, 1.2 g of ansamitocin crystals as a second crop and 3.1 g of a powder from the second mother liquor containing C-15003PND.

EXAMPLE 5

600 ml of ethyl acetate is added to 172 g of the powder of the second mother liquor obtained from crude I by combining the powders produced in 12 batches as described in Examples 3 and 4, followed by stirring and any insoluble materials are removed by filtration. 80 g of neutral alumina (M. Woelm, Germany) is added to the filtrate and, after stirring, ethyl acetate is distilled off under reduced pressure. The residue is placed at the top of a previously prepared alumina column (500 ml) and 500 ml of n-hexane-ethyl acetate (3:1), 700 ml of n-hexane-ethyl acetate (1:1), 1000 ml of n-hexane-ethyl acetate (1:3), 1000 ml of ethyl acetate and 1000 ml of ethyl acetate-methanol (10:1) passed through the column to fractionate the eluate into 200 ml fractions. Each of the fractions is spotted at a position of 2.5 cm from the bottom edge of a silica gel glass plate as described above and developed with a developing solvent, ethyl acetate saturated with water, to a distance of about 17 cm. After development, the adsorbed pattern is analyzed under irradiation with ultraviolet rays and fraction Nos. 13 to 18 showing an absorption at about $R_f$ 0.55 to 0.35 are collected and concentrated to dryness under reduced pressure. 80 ml of ethyl acetate is added to the resulting residue and the mixture allowed to stand to obtain 19.1 g of crystals containing C-15003PND.

EXAMPLE 6

19 g of the crystals obtained as described in Example 5 is dissolved in chloroform and 35 g of silica gel is added thereto. After thorough stirring, chloroform is distilled off under reduced pressure. The residue is placed at the top of 1000 ml of a previously prepared silica gel column and, after washing with 2 l of n-hexane-ethyl acetate (1:1), 6 l of n-hexane-ethyl acetate (1:3), 2 l of n-hexane-ethyl acetate (1:4) and 2 l of ethyl acetate are passed through the column to obtain 400 ml fractions. Each of the fractions is spotted at a position of 2.5 cm from the bottom edge of a silica gel glass plate and developed with a developing solvent, ethyl acetate saturated with water, to a distance of about 17 cm. After development, the adsorbed pattern is analyzed under irradiation with ultraviolet rays and fraction Nos. 8 to 9 which shows an absorption at about $R_f$ 0.55 are collected and concentrated to dryness under reduced pressure to obtain 74 mg of Fraction A containing PND-4. Also, Fraction B (2.3 g) containing PND-3 is obtained from fraction Nos. 10 to 13 which shows an absorption at about $R_f$ 0.48, Fraction C (13.8 g) containing PND-2 is obtained from fraction Nos. 14 to 17 near $R_f$ 0.42, Fraction D (160 mg) containing PND-1 is obtained from fraction Nos. 19 to 21 near $R_f$ 0.37.

EXAMPLE 7

70 mg of Fraction A obtained as described in Example 6 is applied to each of 18 silica gel TLC glass plates as described above in a straight line at a position of 2.5 cm from the bottom edges of the plates and, after development with ethyl acetate saturated with water, the adsorbed pattern at $R_f$ 0.55 is scraped off and extracted twice with ethyl acetate containing a small amount of water. The resulting ethyl acetate extract is washed with water, dried over anhydrous sodium sulfate and concentrated under reduced pressure. Upon addition of petroleum ether to the concentrate, 14 mg of C-15003PND-4 is obtained as a white powder.

EXAMPLE 8

2 g of Fraction B obtained as described in Example 6 is dissolved in 10 ml of methanol and the solution is poured into a preparative high performance liquid chromatograph Prep LC/system 500 (Waters Co., U.S.A.) equipped with a reversed phase gel column (Waters Co., U.S.A., Prep PAK-500/$C_{18}$; 5.7 cm × 30 cm). The solvent, 70% aqueous methanol, is passed through the column at a flow rate of 50 ml/minute and the eluate between 20 and 30 minutes after initiation of elution is fractioned. Methanol is distilled off from the fractions under reduced pressure and the residue is extracted with 150 ml of ethyl acetate. The ethyl acetate extract is dried over anhydrous sodium sulfate and concentrated to dryness under reduced pressure to obtain 123 mg of a white residue. The resulting residue is applied to each of 30 silica gel glass plates as described above in a straight line at a position of 2.5 cm from the bottom edges of the plates and, after development with ethyl acetate saturated with water, the adsorbed patterns at $R_f$0.55 and 0.48 are scraped off and extracted with ethyl acetate containing a small amount of water. The resulting ethyl acetate extract is washed with water, dried over anhydrous sodium sulfate and concentrated under reduced pressure. Upon addition of petroleum ether to the concentrate, 24 mg of C-15003PND-4 as a white powder and 35 mg of PND-3 as a white powder are respectively obtained. Each of the resulting powders of PND-4 and PND-3 is subjected to chromatography using a reversed phase thin-layer glass plate (Merck., Germany; Art. 13724, RP-18 $F_{254}$, 10 × 10) whereby a single adsorbed pattern is observed at $R_f$0.55 and 0.58, respectively, under irradiation with ultraviolet rays.

EXAMPLE 9

13.5 g of Fraction C obtained as described in Example 6 is subjected to preparative high performance liquid chromatography in the same manner as described in Example 8 and the fraction eluted between 20 to 30 minutes after initiation of elution are collected to obtain 1.3 g of a powder. The resulting powder, 1.3 g, is then subjected repeatedly to purification in the same manner as above and 54 mg of a white powder is obtained from the eluates obtained in the same eluting time as that described above. 52 mg of the white powder thus obtained is subjected to preparative TLC in the same manner as described in Example 8 to obtain 13 mg of a white powder of C-15003PND-3 from the adsorbed pattern at $R_f$ 0.48 and 21 mg of a white powder of PND-2 from the adsorbed pattern at $R_f$0.42. Recrystallization of the white powder of C-15003PND-3 from ethyl acetate gives colorless needles. m.p. 217–219.

EXAMPLE 10

130 mg of Fraction D obtained in Example 6 is subjected to preparative high performance liquid chromatography in the same manner as described in Example 8 to obtain 22 mg of a white powder. The product is further subjected to preparative TLC in the same manner as described in Example 8 to obtain 7 mg of a white powder of C-15003PND-1 from the absorbed pattern at $R_f$0.37.

EXAMPLE 11

To 50 ml of chloroform is added 4.7 g of the powders of the crude II obtained in Example 3 and 4, followed by stirring, and insoluble matters are removed by filtration. 3 g of silica gel is added to the filtrate and, after stirring, chloroform is distilled off under reduced pressure. The residue is placed at the top of a previously prepared silica gel column (200 ml), and 200 ml of n-hexane-ethyl acetate (1:4), 200 ml of ethyl acetate and 400 ml of ethyl acetate-methanol (10:1) are passed through the column to fractionate the eluate into 50 ml fractions. Each of the fractions is checked by thin layer chromatography as described in Example 5. Fraction Nos. 13 and 14 showing an absorption at about $R_f$0.25 are collected and concentrated to dryness under reduced pressure. 0.5 ml of methanol is added to the resulting residue and the mixture is allowed to stand to give 42 mg of crystal of PND-0.

REFERENCE EXAMPLE 1

In 0.5 ml of pyridine is dissolved 30 mg of C-15003PND-0, and to the solution is added 0.3 ml of isobutyric anhydride. The mixture is stirred at 22° C. for 18 hours. The reaction mixture is subjected to purification procedure as described in Example 9, whereby 8.5 mg of C-15003PND-3 is obtained.

$[\alpha]_D^{22} - 57.1° \pm 10°(c=0.14$, in methanol)

Ultraviolet absorption spectrum [nm ($\epsilon$), in methanol]: 232(32500), 239(33000), 252(sh 28400), 279(3880), 288(3790).

Infrared absorption spectrum (cm$^{-1}$, KBr): 1740, 1730, 1590, 1455, 1425, 1390, 1145, 1100, 1080.

What we claim is:
1. A compound of the formula:

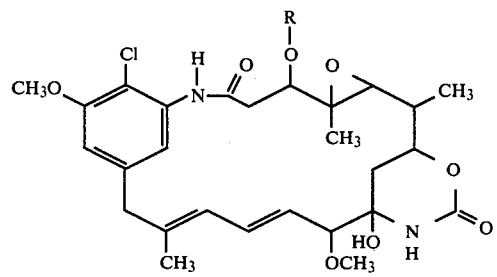

wherein R represents —CO—CH₃, —CO—CH₂—CH₃,

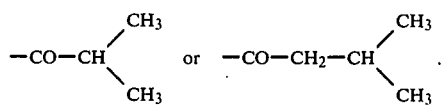

2. A compound as claimed in claim 1, wherein R is —CO—CH₃.
3. A compound as claimed in claim 1, wherein R is —CO—CH₂—CH₃.
4. A compound as claimed in claim 1, wherein R is

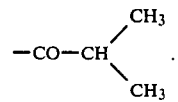

5. A compound as claimed in claim 1, wherein R is

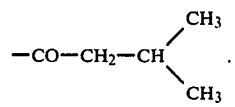

* * * * *

UNITED STATES PATENT AND TRADEMARK OFFICE
CERTIFICATE OF CORRECTION

PATENT NO. : 4,322,348

DATED : March 30, 1982

INVENTOR(S) : M. ASAI ET AL

It is certified that error appears in the above—identified patent and that said Letters Patent is hereby corrected as shown below:

In column 12, please cancel the sentence at lines 35-39.

Signed and Sealed this

Tenth Day of August 1982

[SEAL]

Attest:

Attesting Officer

GERALD J. MOSSINGHOFF

Commissioner of Patents and Trademarks